United States Patent [19]
Secor et al.

[11] Patent Number: 6,133,033
[45] Date of Patent: Oct. 17, 2000

[54] METHOD FOR IN VITRO SELECTION OF POTATO CLONES RESISTANT TO BLACKSPOT BRUISING AND THE POTATOES PRODUCED THEREFROM

[75] Inventors: Gary Allen Secor; Raymond J. Taylor, both of Fargo, N. Dak.; Dennis Lee Bidney, Urbandale, Iowa; Cheryl Louise Ruby, Fargo, N. Dak.

[73] Assignee: J. R. Simplot Company, Boise, Id.

[21] Appl. No.: 09/305,160

[22] Filed: May 4, 1999

Related U.S. Application Data

[63] Continuation of application No. 07/716,115, Jun. 17, 1991, Pat. No. 6,060,312.

[51] Int. Cl.⁷ ...................................................... C12N 5/04
[52] U.S. Cl. ........................... 435/417; 47/58.1; 435/429; 800/200
[58] Field of Search ..................................... 435/417, 429; 800/200; 47/58.1

[56] References Cited

U.S. PATENT DOCUMENTS 5,434,343  7/1995  Johansen .
5,498,541  3/1996  Oka et al. ................................ 435/429

*Primary Examiner*—Leon B. Lankford, Jr.
*Attorney, Agent, or Firm*—Kelly Bauerfeld Lowry & Kelly, LLP.

[57] ABSTRACT

A first method is provided for in vitro selection of Lemhi and Russet Burbank potatoes for blackspot resistance using plant tissue culturing techniques. A second method is provided using at least one melanin precursor added to the tissue culturing media. The blackspot resistant potatoes produced from such methods are also provided.

4 Claims, No Drawings

METHOD FOR IN VITRO SELECTION OF POTATO CLONES RESISTANT TO BLACKSPOT BRUISING AND THE POTATOES PRODUCED THEREFROM

RELATED APPLICATION

This is a continuation of U.S. patent application Ser. No. 07/716,115, filed Jun. 17, 1991.

FIELD OF THE INVENTION

The present invention relates generally to plant tissue culturing for desirable characteristics. More specifically, this invention relates to in vitro selection of Lemhi and Russet Burbank potato clones resistant to blackspot bruising.

BACKGROUND OF THE INVENTION

Blackspot is a physiological (non-infectious) disorder affecting potato tubers damaged during handling. It is also known as blue discoloration, blue spotting, bluing, bruise, internal blackspot, internal bruising, internal grayspot and stem-end blackening. The disorder appears as an internal discoloration and blackening that can be seen when injured tubers are peeled or sliced. The blackening is usually restricted to the outer ¼" to ½" of tuber tissue between the skin and the vascular ring. The color of the spot can vary from a light gray to a blue-gray to an intense coal black. The size and intensity of the spot usually reaches a maximum within 24 hours of bruising and once formed, the blackened area will not disappear.

Blackspot is normally caused by impacts (bumping, dropping, etc.) to the tubers during handling, transportation, storage or packaging but may also be associated to varying degrees with other physical damage such as pressure bruising and/or shatter cracking. The force required to initiate a blackspot need not be severe, particularly to tubers of susceptible cultivars.

The disorder was first reported and described in England in 1912 and since then it has become a serious problem throughout Europe. It was identified in the United States in 1940 and can now be found in all the potato growing areas in this country as well.

Although affected potatoes can be eaten, they are of limited commercial value because of their appearance. The disorder is particularly serious because affected tubers may show no external damage, even after the tuber is washed. Blackspot bruise often results in serious economic losses in both fresh market and processed potatoes, including chips and fries.

Tuber susceptibility and an impact of sufficient magnitude to rupture cells are the two most important factors responsible for initiation and development of blackspot. These conditions activate a series of four biochemical conversions of phenolic compounds (beginning with tyrosine) to conjugated quinones. Intermediate compounds include caffeic acid and p-coumaric acid. This sequence, which is mediated by the action of polyphenyloxidase enzymes, is followed by the polymerization of the quinones to the black pigment melanin. In healthy, non-damaged tissue these phenolic compounds and the polyphenyloxidase enzymes are normally compartmentalized separately and do not come into contact. However, cell rupture causes the contents to mix and the blackening reaction occurs. Although tyrosine and polyphenyloxidase enzymes play a major role in the development of blackspot, the total amount of these compounds present in tubers usually does not correlate with tuber susceptibility or explain differences in blackspot reaction between tubers and cultivars. The most recent work on the biochemistry of blackspot phenomenon indicates that reduction of the free tyrosine pool within the cell increases tuber resistance to blackening. (Corsini et al., Evidence for highly conserved tuber tyrosine levels among potato genotypes and implications for blackspot resistance. Am. Potato J. 66:511–512 (1989)). These investigators found total tyrosine content of many potato cultivars to be remarkably similar though these cultivars ranged widely in their susceptibilities to blackspot. Those cultivars with the greatest resistance to blackspot had a large proportion of the tyrosine bound into protein with very little free tyrosine available for melanin formation. The opposite was found to be true in the susceptible cultivars.

In addition to the biochemical factors discussed above, there are numerous environmental and cultural factors that can contribute to the manifestation of this disorder. Tuber turgor pressure, temperature, specific gravity, mineral nutrition, date of planting, soil moisture, and soil temperature can all influence blackspot development (Hiller et al., Physiological disorders of potato tubers. *Potato Physiology* 389–455, Academic Press, New York (1985)).

Even when all the predisposing factors are considered, potato cultivars vary markedly in their response to impact damage. Some cultivars may be highly resistant to blackspot while others may be highly susceptible. Tubers from a single plant may differ in their blackening responses. Susceptibility may also vary from the stem end to bud end of an individual tuber.

Losses due to blackspot can be managed to a certain extent by production practices employed during the growing season. Practices currently employed to control blackspot bruising are to keep the plants as healthy as possible by providing adequate disease and pest control, and good soil moisture and soil fertility (particularly potassium). Soil should not be allowed to dry out prior to harvest and vines should be killed early to reduce water loss from the tubers. The most important means of controlling the extent of blackspot formation is reducing tuber injury both during and after harvest. This can be implemented by not harvesting tubers when the soil temperature is low (8° C.) and by adjusting operation speeds, drop lengths and padding on all potato handling equipment. Selection of cultivars that are more resistant to blackspot is also an important consideration. However, this is not always possible because of production restrictions. Some cultivars demonstrate great potential for commercial production but suffer because of blackspot bruising. Such is the case with the cultivar Lemhi Russet and to a lesser extent, Russet Burbank.

'Lemhi' and Russet Burbank have many characteristics that make them suitable and important cultivars for the processing industry, including low reducing sugar levels, good storability, excellent processing and dormancy. However, they are extremely susceptible to blackspot. Naturally resistant Lemhi and Russet Burbank have not been found. This limits their acceptability because the quality of processed products (e.g. chips and fries) obtained from bruise-damaged potatoes is lowered substantially. Although resistance to blackspot may be attainable through traditional breeding techniques, other characters which make the cultivar commercially acceptable, such as sugar levels, shape, specific gravity, or yield, could also change. It is difficult to maintain every desirable character while breeding for cultivar improvement and such an approach would involve several years of crossing and testing.

As an alternative to traditional breeding techniques, plant cell culture provides the opportunity to evaluate large quantities of cells (literally millions), having the potential of regeneration into valuable somaclonal variants. Normally, a large population of regenerated plants is required in order to identify somaclones with the desired traits. Increasing and testing such populations is labor intensive and requires a tremendous amount of greenhouse and field space. This problem is usually addressed by developing techniques that will allow the somaclones to be screened for the required characteristic(s) while in tissue culture, prior to being regenerated into plants. Evaluation at the cell culture level greatly reduces space involved and increases the number of somaclonal lines that can be examined. In vitro screening procedures essentially increase the likelihood of identifying clones with desirable traits by eliminating unwanted material. Accordingly, there is a need to provide an alternative to a traditional breeding approach for potato cultivar improvement and development. There is also a need for increasing the likelihood of identifying blackspot resistant 'Lemhi' and Russet Burbank potato clones. There is further a need for techniques which increase the ease and efficiency of identifying and selecting prospective blackspot resistant 'Lemhi' and Russet Burbank somaclones. The present invention fulfills these needs and provides other related advantages.

SUMMARY OF THE INVENTION

The present invention resides in methods for in vitro selection of 'Lemhi' and Russet Burbank for blackspot resistance using plant tissue culturing techniques and using at least one melanin precursor, such as tyrosine or caffeic acid, added to the tissue culturing media. The present invention also resides in the blackspot resistant tubers produced from the in vitro selection. The methods are based upon in vitro somatic cell isolation, culture, screening, selection, and regeneration, not involving sexual crossing.

The methods comprise, generally, culturing tissue obtained from a potato plant in cell layer and associated reservoir media, subculturing the tissue on callus proliferation medium to obtain callus formation, subculturing the callus on shoot induction medium to obtain shoot formation and subculturing the shoot on a rooting medium to ensure root formation, whereby potato plants are regenerated from which blackspot resistant tubers are produced. At least one melanin precursor may be added to the reservoir, callus proliferation and rooting medium to further increase the likelihood of identifying blackspot resistant clones. When the melanin precursor screening method is used, potato plants are regenerated from the calli and roots which show no blackening response when the melanin precursor is present in the various media.

Other features and advantages of the present invention will become apparent from the following more detailed description.

DETAILED DESCRIPTION OF THE PREFERRED EMBODIMENTS

This invention provides methods for increasing the quantity of regenerated Lemhi and Russet Burbank potato clones having increased resistance to blackspot and the potato tubers produced therefrom.

Procedures For The Collection. Culture. And Regeneration Of Potato Mesophyll Protoplasts The following procedures should be viewed with reference to the abbreviations and compositions that follow:

List of Abbreviations

BAP 6-benzylaminopurine
GA$_3$ gibberellic acid
NAA naphthaleneacetic acid
MES 2[N-morpholino]ethanesulfonic acid
PVP-10 polyvinylpyrrolidone (10,000 MW)
EDTA ethylenediaminetetraacetic acid (sodium salt)

| Composition of Major Salts Stock | |
|---|---|
| KNO$_3$ | 19.0 g/l |
| CaCl$_2$ * 2H$_2$O | 4.4 |
| MgSO$_4$ * 7H$_2$O | 3.7 |
| KH$_2$PO$_4$ | 1.7 |
| Composition of Minor Elements (Stock I) | |
| H$_3$BO$_4$ | 0.620 g/l |
| MnCl$_2$ * 4H$_2$O | 1.980 |
| ZnSO$_4$ * 7H$_2$O | 0.920 |
| Composition of Minor Elements (Stock II) | |
| KI | 0.083 g/l |
| Na$_2$MoO$_4$ * 2H$_2$O | 0.025 |
| CuSO$_4$ * 5H$_2$O | 0.0025 |
| CoSO$_4$ * 7H$_2$O | 0.003 |
| Composition of Organics Stock | |
| myo-Inositol | 20.0 g/l |
| Thiamine * HCl | 0.1 |
| Glycine | 0.4 |
| Nicotinic Acid | 1.0 |
| Pyridoxine * HCl | 0.1 |
| Folic Acid | 0.1 |
| Biotin | 0.01 |
| Composition of Fe-EDTA Stock | |
| Na$_2$ EDTA | 0.373 g/l |
| FeSO$_4$ * 7H$_2$O | 0.278 |
| Composition of Miscellaneous Stocks | |
| Casein Hydrolysate | 10.0 mg/ml |
| NH$_4$Cl | 0.1M |
| MES | 0.5M |
| Composition of Plant Growth Regulator Stocks | |
| BAP, GA$_3$, NAA and Zeatin stocks at 0.1 mg/ml. | |

Growth of Source Plants

Potato tubers should be maintained at room temperature to break dormancy. This usually occurs within 7 to 14 days. After sprouting is initiated, the tubers are planted individually in 20 cm clay pots containing an artificial soil mix such as Jiffy-Mix (JPA, 1400 Harvester Rd., West Chicago, Ill. 60185) or Sunshine Mix (Fisons Western Corporation, Vancouver, BC Canada V6H 3V1). The soil should be kept moist with distilled water but overwatering should be avoided. The sprouts are excised from the mother tuber when they are 6–10 cm high and planted in individual 20 cm clay pots containing the soil mix. The plants should be grown at 70–80% relative humidity in a controlled environment chamber illuminated with cool white fluorescent light under a 12 hour photoperiod. The light regime should consist of 5 hr illumination at 90uE m$^{-2}$ sec$^{-1}$ and 2 hr at 325 uE m$^{-2}$ sec$^{-1}$, followed by 5 hr at 90 uE m$^{-2}$ sec$^{-1}$. The temperature is maintained at 16° C. except for hours two through six of the light period when it is increased to 22° C. Plants are fertilized biweekly as described by Shepard, J. F., Mutant selection and plant regeneration from potato mesophyll protoplasts, Genetic Improvement of Crops: Emergent Techniques. University of Minnesota Press, pp.185–219 (1980).

Protoplast source plants can also be produced from plants initiated from meristem cultures and increased via nodal cuttings. They can be grown and maintained on medium E under the conditions described later in the Plant Regeneration Sequence section dealing with shoot elongation/root initiation.

Protoplast Isolation (leaf harvest)

Protoplast yields are fairly consistent when leaflets are collected from plants 4–8 weeks after transplanting. The leaves are excised from nodal position 3–7 (from top of plant). The use of very young leaves or very old leaves should be avoided. Leaves with large terminal leaflets (>5 cm) generally yield large quantities of protoplasts. The largest leaflets are selected. A portion of the petiole attached to each leaflet is left there to facilitate handling. Approximately 3.5–4.5 g of leaf tissue (5–6 leaflets) will usually provide enough cells to work with. After the fresh weight is determined, the leaflets are ready to be preconditioned for enzyme isolation.

Protoplast Isolation (leaflet preconditioning)

Utmost care must be taken to assure that conditions of absolute sterility are maintained throughout all of the in vitro manipulations described below. The leaflets must be sterilized before they are placed in the conditioning solutions. Each leaflet is dipped in 70% ethyl alcohol (1–2 sec), then transferred to a beaker containing 1000 ml of a 10% bleach (Chlorox, Hilex, etc.) solution. The leaflets are kept submerged in the hypochlorite solution for 2–3 minutes and then transferred to a beaker containing 500 ml of sterile, distilled water. Each leaflet is dipped in the water approximately 10 times to rinse and then transferred to a second beaker containing sterile, distilled water and the rinse procedure repeated. After the second rinse, the leaflets are dipped in 70% ethyl alcohol (1–2 sec). The leaflets are now ready for the conditioning solutions. 250 ml of sterile float solution is aseptically transferred to a large (20 cm), covered, glass wash bowl (sterile).

| FLOAT SOLUTION | |
|---|---|
| $NH_4NO_3$ | 80 mg |
| $CaCl_2 * H_2O$ | 147 mg |
| NAA (2 mg/l) | 20 ml stock |
| BAP (1 mg/l) | 10 ml stock |
| Volume to 1000 ml | |
| Autoclave | |

The leaflets are floated abaxial (top) side down on the surface of the float solution. The bowl is covered with foil and incubated at 24° C. for 48 hours. After incubation, the leaflets are removed and the surface sterilization procedure described above is repeated. After the final 70% ethyl alcohol dip, the leaflets are allowed to air dry on sterile paper towels in a laminar flow hood.

A nylon bristled artist's brush is sterilized by immersing it in 95% ethyl alcohol for 5–10 minutes. The brush is allowed to air dry, and the adaxial (lower) surface of each leaflet is carefully brushed. The brushing motion should be toward the leaflet tip and should be continued until the epidermis has been stripped from the leaflet. The stripping procedure is completed when the tissue changes from light to dark green. The midvein from each leaflet is removed and discarded. The brushed tissue is aseptically cut into narrow strips (1–3 mm wide) and transferred to a 500 ml sidearm flask containing 200 ml of sterile soak solution. The flask is swirled to uniformly distribute tissue slices throughout the solution. The flask is covered with foil and incubated at 4° C. to 10° C. for 24 hours.

| SOAK SOLUTION | |
|---|---|
| Major Salts | 2.5 ml stock |
| Fe-EDTA | 2.5 ml stock |
| Organics | 0.25 ml stock |
| Minors I | 0.25 ml stock |
| Minors II | 0.25 ml stock |
| $NH_4Cl$ | 1.0 ml stock |
| NAA | 2.0 ml stock |
| BAP | 1.0 ml stock |
| Volume to 200 ml | |
| pH 5.6 | |
| Autoclave | |

Protoplast Isolation (leaflet digestion)

After the soak stage is completed, the liquid is carefully decanted from the flask and replaced with 100 ml of enzyme solution.

| ENZYME SOLUTION | |
|---|---|
| Yakult Macerozyme R-10 | 0.1 g |
| Yakult Cellulase RS | 0.5 g |
| Major Salts | 5.0 ml stock |
| MES | 1.0 ml stock |
| PVP-10 | 1.0 g |
| Casein Hydrolysate | 1.0 mg |
| Sucrose | 10.27 g |
| $NH_4Cl$ | 0.5 ml stock |
| Volume to 100 ml | |
| pH 5.6 | |
| Filter Sterilize | |

The leaflet section is vacuum infiltrated (25–27 inches Hg) for 7 minutes and the flask is placed on a gyratory shaker (100 RPM) and incubated at room temperature (27° C.) until the tissue has disassociated (3–5 hours). The digestion time varies with cultivar, age of tissue, temperature, shaker speed, and specific gravity of the enzyme solution.

Protoplast Isolation (protoplast harvest)

The protoplasts (cells with the cell wall removed) are collected by centrifugal flotation in sterile Babcock (milk test) bottles. The contents of the digestion flask are gently poured into a sterile funnel containing several layers of cheesecloth. The funnel tip is fitted with a 5¼ inch Pasteur pipet via a piece of plastic tubing. The pipet tip should rest against the inside of the Babcock bottle neck about ½ to ⅓ of the distance from the mouth. Protoplasts are extremely fragile so the protoplast suspension should flow down the sides and not splash directly to the bottom of the bottle. Freshly isolated protoplasts are also light sensitive so the collection procedure should be carried out under subdued light. A sterile rinse solution is poured through the debris lodged in the cheesecloth filter while gently shaking the filter with the tip of a pipet.

| RINSE SOLUTION | |
| --- | --- |
| Major Salts | 10.0 ml stock |
| Casein Hydrolysate | 1.0 ml stock |
| Sucrose | 20.54 g |
| $NH_4Cl$ | 1.0 ml stock |
| Volume to 200 ml | |
| pH 5.6 | |
| Filter Sterilize | |

The debris is rinsed until 3 Babcock bottles are filled. A fourth bottle is filled with sterile rinse solution. This bottle is used to balance the centrifuge. The bottles are centrifuged at 500 RPM for 10 minutes (IEC HN-SII centrifuge with rotor 215 and carriers 367A). The debris is spun to the bottom of the bottles and intact protoplasts float to the top. 5–10 ml of sterile rinse is removed from the balance bottle. The protoplast layer from each of the other bottles is transferred to the rinse bottle with a sterile 9 inch Pasteur pipet. The pipet tip is submerged in the rinse solution then the protoplasts are slowly and gently forced into the solution. The bottle is tilted at approximately a 45 degree angle and rotated for several minutes to distribute the protoplasts evenly throughout the rinse solution. Fresh rinse solution is added to bring the volume up to the top gradation on the Babcock bottle neck (#8) and centrifuged again. The resultant floating protoplasts may now be plated if 1× salts are used in the CL medium. If 4× salts are included in the CL medium, the protoplasts must be acclimated in a holding solution for at least 1 hour prior to plating.

| HOLDING SOLUTION | |
| --- | --- |
| Major Salts | 20.0 ml stock |
| Fe-EDTA | 5.0 ml stock |
| Minors I | 0.5 ml stock |
| Minors II | 0.5 ml stock |
| Casein Hydrolysate | 0.1 ml stock |
| Sucrose | 6.8 g |
| Inositol | 0.45 g |
| Xylitol | 0.45 g |
| Sorbitol | 0.455 g |
| Mannitol | 0.455 g |
| Volume to 100 ml | |
| pH 5.6 | |
| Filter Sterilize | |

The number of divisions occupied by the protoplast layer is read off the bottle neck to estimate the number of cells collected (one large division contains approximately 2.5 million protoplasts). The inside of a sterile Pasteur pipet is coated with holding solution by rinsing several times and drawing off the protoplast layer and then diluting the protoplasts with holding solution to a concentration of 1 million cells/ml. The protoplasts are maintained in holding solution at 22–24 C° for a minimum of 1 hour.

Method for In Vitro Selection of Black Spot Resistant Protoplast-derived Potato Clones Plant Regeneration Sequence (protoplast culture)

Protoplasts are cultured in plastic quadrant plates. The plates are prepared by making a slit with an electric soldering gun along the base of each divider. Each of two opposite sectors are filled with 10 ml of R medium.

| R MEDIUM | |
| --- | --- |
| Major Salts | 50.0 ml stock |
| $NH_4Cl$ | 5.0 ml stock |
| Fe-EDTA | 50.0 ml stock |
| Minors I | 5.0 ml stock |
| Minors II | 5.0 ml stock |
| Organics | 5.0 ml stock |
| Casein Hydrolysate | 100.0 mg |
| Mannitol | 18.2 g |
| Sucrose | 34.2 g |
| NAA | 10.0 ml stock |
| BAP | 4.0 ml stock |
| Difco Purified Agar | 6.0 g |
| Volume to 1000 ml | |
| pH 5.6 | |
| Autoclave | |

The working concentrations of the R Medium are as follows:

| R Medium - Working Concentrations | |
| --- | --- |
| $NH_4Cl$ | 27 mg/l |
| Major Salts | |
| $KNO_3$ | 950 mg/l |
| $CaCl_2 * 2H_2O$ | 220 |
| $MgSO_4 * 7H_2O$ | 185 |
| $KH_2PO_4$ | 85 |
| Iron and Minor Elements | |
| $Na_2 * EDTA$ | 18.5 mg/l |
| $FeSO_4 * 7H_2O$ | 13.9 |
| $H_3BO_4$ | 3.1 |
| $MnCl_2 * 4H_2O$ | 9.9 |
| $ZnSO_4 * 7H_2O$ | 4.6 |
| KI | 0.42 |
| $Na_2MoO_4 * 2H_2O$ | 0.13 |
| $CuSO_4 * 5H_2O$ | 0.013 |
| $CoSO_4 * 7H_2O$ | 0.015 |
| Organics | |
| Thiamine * HCl | 0.5 mg/l |
| Glycine | 2.0 |
| Nicotinic Acid | 5.0 |
| Pyridoxine * HCl | 0.5 |
| Folic Acid | 0.5 |
| Biotin | 0.05 |
| Casein Hydrolysate | 100.0 |
| Osmoticum | |
| Sucrose | 0.1M |
| Mannitol | 0.1 |
| Other | |
| NAA | 1.0 mg/l |
| BAP | 0.4 mg/l |
| Agar | 0.6% |
| pH | 5.6 |

The protoplast cell layer medium (CL medium) is prepared by mixing 4 parts SLLX solution with one part of the CL component.

| SLLX | |
| --- | --- |
| Major Salts | 50.0 ml stock |
| Sucrose | 0.56 g |
| Inositol | 0.56 g |

-continued

| | | |
|---|---|---|
| Xylitol | 0.56 g | |
| Sorbitol | 0.56 g | |
| Mannitol | 0.56 g | |
| Volume to 100 ml | | |
| pH 5.6 | | |
| Filter Sterilize | | |
| CL | | |
| Fe-EDTA | 6.25 | ml stock |
| Minors I | 0.625 | ml stock |
| Minors II | 0.625 | ml stock |
| Casein Hydrolysate | 0.625 | ml stock |
| NAA | 1.25 | ml stock |
| BAP | 0.5 | ml stock |
| Agarose (Type VII) | 0.56 g | |
| Volume to 25 ml | | |
| pH 5.6 | | |
| Autoclave | | |

The working concentrations of the CL medium are set forth below:

| CL Medium - Working Concentrations | |
|---|---|
| Major Salts | |
| $KNO_3$ | 7600 mg/l |
| $CaCl_2 * 2H_2O$ | 1760 |
| $MgSO_4 * 7H_2O$ | 1480 |
| $KH_2PO_4$ | 680 |
| Iron and Minor Elements | |
| $Na_2 * EDTA$ | 18.5 mg/l |
| $FeSO_4 * 7H_2O$ | 13.9 |
| $H_3BO_4$ | 3.1 |
| $MnCl_2 * 4H_2O$ | 9.9 |
| $ZnSO_4 * 7H_2O$ | 4.6 |
| KI | 0.42 |
| $Na_2MoO_4 * 2H_2O$ | 0.13 |
| $CuSO_4 * 5H_2O$ | 0.013 |
| $CoSO_4 * 7H_2O$ | 0.015 |
| Organics | |
| Thiamine * HCl | 0.5 mg/l |
| Glycine | 2.0 |
| Nicotinic Acid | 5.0 |
| Pyridoxine * HCl | 0.5 |
| Folic Acid | 0.5 |
| Biotin | 0.05 |
| Casein Hydrolysate | 50.0 |
| Osmoticum | |
| Sucrose | 0.200M |
| Mannitol | 0.025 |
| myo-Inositol | 0.025 |
| Sorbitol | 0.025 |
| Xylitol | 0.025 |
| Other | |
| NAA | 1.0 mg/l |
| BAP | 0.4 mg/l |
| Agarose (type VII) | 0.45% |
| pH | 5.6 |

The mixed CL/SLLX medium is allowed to cool to room temperature (10–15 minutes). Then, the protoplast suspension is diluted to the desired concentration (20,000–40,000 cells/ml). Using a sterile pipet tip, the protoplasts are gently mixed to a uniform suspension in the medium. 3 ml of the suspension is transferred to each of the empty quadrant plate sectors for a total of 6 ml per plate. The plates are sealed with Parafilm® and incubated at 24° C. for 10–14 days under constant illumination (cool, white fluorescent light). Low light intensity (approximately 600 lux) is required during this initial growth phase.

Plant Regeneration Sequence (callus culture)

The cell layer in gel form is cut into sections with a sterile spatula and these gel slabs are transferred to Petri plates, each containing 20 ml of C medium (=Cl) (callus proliferation medium). The entire contents of one quadrant should be layered on each C medium plate. The plates are sealed with Parafilm® and incubated at 24° C. under constant illumination of approximately 3000 lux (cool, white fluorescent light). After 2–3 weeks, the calli (small aggregates of cells) should be light green and about 1–2 mm in diameter. Individual calli are picked from the gel with the tip of a sterile scalpel blade and transferred to a plate containing fresh C medium (25–50 calli/plate). These C medium plates (=C2) are incubated as directed above.

| C MEDIUM | | |
|---|---|---|
| Major Salts | 100.0 | ml stock |
| $NH_4Cl$ | 20.0 | ml stock |
| Fe-EDTA | 50.0 | ml stock |
| Minors I | 5.0 | ml stock |
| Minors II | 5.0 | ml stock |
| Organics | 5.0 | ml stock |
| Casein Hydrolysate | 400.0 | mg |
| Adenine Sulfate | 40.0 | mg |
| Mannitol | 54.6 | g |
| Sucrose | 2.5 | g |
| NAA | 1.0 | ml stock |
| BAP | 5.0 | ml stock |
| MES | 10.0 | ml stock |
| Difco Purified Agar | 9.0 | g |
| Volume to 1000 ml | | |
| pH 5.6 | | |
| Autoclave | | |

The working concentrations of the C medium are set forth below:

| C medium - Working Concentrations | |
|---|---|
| $NH_4Cl$ | 107 mg/l |
| Major Salts | |
| $KNO_3$ | 1900 mg/l |
| $CaCl_2 \cdot _{2H_2}O$ | 440 |
| $MgSO_4 \cdot _{7H_2}O$ | 370 |
| $KH_2PO_4$ | 170 |
| Iron and Minor Elements | |
| $Na_4 * EDTA$ | 18.5 mg/l |
| $FeSO_4 \cdot _{7H_2}O$ | 13.9 |
| $H_3BO_4$ | 3.1 |
| $MnCl_2 \cdot _{4H_2}O$ | 9.9 |
| $ZnSO_4 \cdot _{7H_2}O$ | 4.6 |
| KI | 0.42 |
| $Na2MoO_4 * 2H_2O$ | 0.13 |
| $CuSO_4 \cdot _{5H_2}O$ | 0.013 |
| $CoSo4 * 7H_2O$ | 0.015 |
| Organics | |
| Myo-Inositol | 100.0 mg/l |
| Thiamine * HCl | 0.5 |
| Glycine | 2.0 |
| Nicotinic Acid | 5.0 |
| Pyridoxine * HCl | 0.5 |
| Folic Acid | 0.5 |
| Biotin | 0.05 |
| Casein Hydrolysate | 100.0 |

-continued

| C medium - Working Concentrations | |
|---|---|
| Adenine Sulfate | 40.0 |
| Osmoticum | |
| Sucrose | 0.25% |
| Mannitol | 0.3M |
| Other | |
| NAA | 0.1 mg/l |
| BAP | 0.5 mg/l |
| MES | 5.0 mM |
| Agar | 0.9% |
| pH | 5.6 |

Plant Regeneration Sequence (callus differentiation)

The calli from the C medium plates are transferred to plates containing shoot induction medium (6D medium) (10–25 calli/plate) when the calli become dark green (3–5 weeks). The plates are sealed with Parafilm® and incubated at 24° C. under cool, white fluorescent light (3000–4000 lux) with a diurnal cycle of 16 hours light/8 hours dark. Shoot induction usually occurs after 6–8 weeks. However, some cultivars only produce shoots after long term culture (6–8 months) on shoot regeneration medium.

| 6D MEDIUM | |
|---|---|
| Major Salts | 100.0 ml stock |
| $NH_4Cl$ | 50.0 ml stock |
| Fe-EDTA | 50.0 ml stock |
| Minors I | 5.0 ml stock |
| Minors II | 5.0 ml stock |
| Organics | 5.0 ml stock |
| Casein Hydrolysate | 100.0 mg |
| Adenine Sulfate | 80.0 mg |
| Mannitol | 36.4 g |
| Sucrose | 2.5 g |
| Zeatin (trans isomer) | 20.0 ml stock |
| NAA | 0.1 ml stock |
| $GA_3$ | 0.1 ml stock |
| MES | 10.0 ml stock |
| Difco Purified Agar | 10.0 g |
| Volume to 1000 ml | |
| pH 5.6 | |
| Autoclave | |
| Zeatin & $GA_3$ added after autoclave | |

The working concentrations of the 6D medium are set forth below:

| 6D Medium - Working Concentrations | |
|---|---|
| $NH_4Cl$ | 267.5 mg/l |
| Major Salts | |
| $KNO_3$ | 1900 mg/l |
| $CaCl_2 * 2H_2O$ | 440 |
| $MgSO_4 * 7H_2O$ | 370 |
| $KH_2PO_4$ | 170 |
| Iron and Minor Elements | |
| $Na_2 * EDTA$ | 18.5 mg/l |
| $FeSO_4 * 7H_2O$ | 13.9 |
| $H_3BO_4$ | 3.1 |
| $MnCl_2 * 4H_2O$ | 9.9 |
| $ZnSO_4 * 7H_2O$ | 4.6 |

-continued

| 6D Medium - Working Concentrations | |
|---|---|
| KI | 0.42 |
| $Na_2MoO_4 * 2H_2O$ | 0.13 |
| $CuSO_4 * 5H_2O$ | 0.013 |
| $CoSO_4 * 7H_2O$ | 0.015 |
| Organics | |
| Myo-Inositiol | 100.0 mg/l |
| Thiamine * HCl | 0.5 |
| Glycine | 2.0 |
| Nicotinic Acid | 5.0 |
| Pyridoxine * HCl | 0.5 |
| Folic Acid | 0.5 |
| Biotin | 0.05 |
| Casein Hydrolysate | 100.0 |
| Adenine Sulfate | 80.0 |
| Osmoticum | |
| Sucrose | 0.25% |
| Mannitol | 0.2M |
| Other | |
| Zeatin (trans isomer) | 2.0 mg/l |
| NAA | 0.01 |
| $GA_3$ | 0.01 |
| MES | 5.0 mM |
| Agar | 1.0% |
| pH | 5.6 |

Plant Regeneration Sequence (shoot elongation/root initiation)

The shoots from individual calli are excised when they are 2–10 mm long and transferred to glass test tubes (25×150 mm) containing 15 ml of E medium. The base of each shoot is pushed into the medium, the tubes capped and sealed with filter tape. The tubes are incubated at 24° C. under cool, white fluorescent light (1500–2000 lux with a daily 8 hour dark period). Root initiation should occur within 2–5 weeks.

| E MEDIUM | |
|---|---|
| Major Salts | 100.0 ml stock |
| $NH_4Cl$ | 50.0 ml stock |
| Fe-EDTA | 50.0 ml stock |
| Minors I | 5.0 ml stock |
| Minors II | 5.0 ml stock |
| Organics | 5.0 ml stock |
| Adenine Sulfate | 40.0 mg |
| Sucrose | 6.0 g |
| MES | 10.0 ml stock |
| Difco Purified Agar | 5.0 g |
| Volume to 1000 ml | |
| pH 5.6 | |
| Autoclave | |

The working concentrations of the E Medium are as follows:

| E Medium - Working Concentrations | |
|---|---|
| $NH_4Cl$ | 267.5 mg/l |
| Major Salts | |
| $KNO_3$ | 1900 mg/l |
| $CaCl_2 * 2H_2O$ | 440 |
| $MgSO_4 * 7H_2O$ | 370 |

-continued

E Medium - Working Concentrations

| | |
|---|---|
| $KH_2PO_4$ | 170 |
| Iron and Minor Elements | |
| | |
| $Na_2$ * EDTA | 18.5 mg/l |
| $FeSO_4$ * $7H_2O$ | 13.9 |
| $H_3BO_4$ | 3.1 |
| $MnCl_2$ * $4H_2O$ | 9.9 |
| $ZnSO_4$ * $7H_2O$ | 4.6 |
| KI | 0.42 |
| $Na_2MoO_4$ * $2H_2O$ | 0.13 |
| $CuSO_4$ * $5H_2O$ | 0.013 |
| $CoSO_4$ * $7H_2O$ | 0.015 |
| Organics | |
| | |
| Myo-Inositol | 100.0 mg/l |
| Thiamine * HCl | 0.5 |
| Glycine | 2.0 |
| Nicotinic Acid | 5.0 |
| Pyridoxine * HCl | 0.5 |
| Folic Acid | 0.5 |
| Biotin | 0.05 |
| Adenine Sulfate | 40.0 |
| Osmoticum | |
| | |
| Sucrose | 1.0% |
| Mannitol | 0.1M |
| Other | |
| | |
| Agar | 0.5% |
| pH | 5.6 |

Plant Regeneration Sequence (growth of regenerated plantlets)

The plantlets are removed from the tubes and the roots washed free of agar with distilled water. Each plantlet is transferred to an 8 cm clay pot containing Jiffy-Mix. The pots are watered with approximately 100 ml of Peters 20-20-20 fertilizer (0.5 g/l). Each pot is sealed inside a clear plastic bag. Bagged pots are incubated under fluorescent lights at room temperature (22–27° C.). After one week, the tops of the bags are opened. The openings are increased over the next 7 to 10 days, after which the bags can be removed entirely. The plants are allowed to grow for an additional 2–4 weeks. When the plants are 15–25 cm tall, they should be transplanted to larger clay pots (20–30 cm) containing Jiffy-Mix. The plants are then grown in the greenhouse until tuber set is complete (2–4 months). About one week before harvesting, the vines are cut and the soil in the pots allowed to dry. The tubers from each protoplast-derived clone are collected in paper bags and stored under refrigeration for field increase.

The techniques described above are based upon the procedures described by Shepard, J. F. Mutant selection and plant regeneration from potato mesophyll protoplasts, Genetic Improvement of Crops: Emergent Techniques. University of Minnesota Press, pp. 185–219 (1980) as modified by Taylor, R. J. and Secor, G. A., A shoot induction procedure altered for increased shoot efficiency of potato protoplast—derived calli, *Potato Research* 31:651–658 (1988), and incorporated by reference herein.

In a preferred embodiment, potato mesophyll protoplasts are collected, cultured, and regenerated according to the procedures described above except that at least one melanin precursor such as tyrosine or caffeic acid is included in some of the tissue culture media. This method allows for additional increases in the number of clones resistant to blackspot. The culture induced screening method without at least one melanin precursor, as described above itself results in some blackspot resistant clones.

At Stage 1 of the melanin precursor screening method, protoplasts are diluted (40,000 cells/ml) in normal CL medium (melanin precursor-free) and then transferred to culture plates containing R medium (reservoir medium) with tyrosine or caffiec acid at 0.25 mM. After the normal incubation period, the protoplasts and protoplast-derived micro calli are transferred, along with the cell layer medium (CL), to C medium containing tyrosine at 0.5 mM. This first transfer to C medium is Stage 2 of the process. After the standard incubation period, only individual calli showing no blackening response are selected and transferred to fresh C medium containing tyrosine or caffeic acid at 1.0 mM for Stage 3 screening. The calli are incubated for an additional 2–4 weeks and those that remain green (no blackening evident) are wounded by cutting with a sterile scalpel blade. After 24 hours the cut calli are evaluated for blackening in the wounded area. After this Stage 4 screen, only the surviving green calli are transferred to normal 6D medium (shoot induction medium) (without melanin precursor) for plantlet initiation. Regenerated shoots are transferred to E medium (rooting medium) containing tyrosine or caffeic acid at 0.5 mM for the final (Stage 5) screen. All shoots that develop roots which do not exhibit blackening in the medium are rescued as potential blackspot resistant clones. These plants are transplanted to individual pots and grown in the greenhouse for tuber production. Each plant normally produces from 6–24 tubers which are maintained until the following field growing season. Tubers of the selected clones are subsequently increased 1 or 2 field generations. Anatomical characteristics of the clones are examined in both the greenhouse and the field and harvested tubers are tested for blackspot bruising. It may be advantageous to add tyrosine or caffeic acid at only some of the stages as the protoplasts and calli may otherwise become damaged and thus unusable.

TABLE 1: Summary of the minimum time involved in screening and regeneration sequences.

| STAGE | Duration | Cumulative Time |
|---|---|---|
| Plantlet Regeneration | | |
| | | |
| CL/R Screen (1) | 10 days | 10 days |
| C1 Screen (2) | 10 days | 20 days |
| C2 Screen (3) | 21 days | 41 days |
| C2 Screen (4) | 1 day | 42 days |
| 6D Regeneration | 45 days | 87 days |
| E Screen (5) | 21 days | 108 days |
| Tuber Production | | |
| | | |
| (lab preconditioning) | 14 days | 122 days |
| (greenhouse) | 90 days | 212 days |

Discussion

The procedure for identifying cells and calli that could yield plants resistant to blackspot is based upon the biochemical processes that normally occur in bruised tubers. Tyrosine, which is the principle compound converted to the black pigment melanin through a series of biochemical reactions, or caffeic acid, an intermediate compound in the melanin pathway, are included as additional components in the standard tissue culture media described above. Calli derived from individual protoplasts are evaluated for the production of black pigmentation at several stages during the tissue culture process. Those that demonstrate a blackening response in the presence of tyrosine or caffeic acid are rejected as presumed suscepts and those that show no blackening throughout the growth and regeneration process are retained as potential resistant clones. Plants produced from such calli are carried through greenhouse and field increase in order to produce sufficient quantities of tubers for subsequent bruising and blackspot evaluation.

Blackspot Testing (methods and rating system used)

Tubers are bruised under controlled conditions using an apparatus similar to the one described by Kunkel et al., Improvements of techniques for blackspot evaluation and some errors associated with measurements. *Am. Potato J.* 63: 13–23 (1986), said description incorporated herein by reference. Five tubers from each clone were tested by striking them with a 115 g weight dropped from a height of 45 or 50 cm, with each tuber receiving 9 impacts (3 stem end, 3 middle, 3 bud end). The tubers were maintained at 75° C. for 24 hours, and then evaluated. In year 1 of testing, the quantity of available tubers regenerated was minimal due to environmental conditions. In years 1 and 3, 5 tubers from each clone were tested at 9 impacts per tuber for a total of 45 bruise spots. In year 2, testing was repeated 3 times for each clone (15 tubers/clone) at 9 impacts per tuber for a total of 135 bruise spot, The results shown below for year 2 reflect the average from three trials. For some clones, year 2 was the first year of testing for that clone. Blackspot development was determined visually by slicing through the impact areas with a knife. Thin tissue slices were removed parallel to the tuber surface until maximum diameter and blackening intensity were attained.

Three criteria are used to quantify blackspot susceptibility: (1) The severity (S) of bruising at each impact point was rated according to a 5 point scale where:

0=no spot development
1=very small spot with a trace of blackening
2=small spot with limited blackening
3=moderate spot with moderate blackening
4=large black spot
5=very large spot with intense blackening (2) The spots were counted and the percentage (PC) of impact areas that developed spots is determined from this information. (3) A blackspot index (BI) is calculated from the above information according to the following formula:

$$BI = S \times PC$$

Susceptibility/resistance of a cultivar is expressed as an average blackspot index calculated from all bruised tubers.

Summary Table

| Treatment | Resistant*/Total | % Resistant |
|---|---|---|
| Culture-induced Screening | | |
| Year 1 | 8/22 | 36.4 |
| Year 2 | 12/38 | 31.6 |
| Year 3 | 7/26 | 26.9 |
| | | Mean: 31.6 |
| Screened with Melanin Precursors | | |
| Year 1 | 5/7 | 71.42 |
| Year 2 | 21/40 | 52.5 |
| Year 3 | 22/49 | 44.9 |
| | | MEAN: 56.3 |
| Screened with Caffeic Acid | | |
| Year 1 | 5/7 | 71.42 |
| Year 2 | 3/9 | 33.3 |
| Year 3 | 3/9 | 33.3 |
| | | MEAN: 46.0 |
| Screend with Tyrosine | | |
| Year 1 | — | |
| Year 2 | 18/31 | 58.1 |
| Year 3 | 19/40 | 47.5 |
| | | MEAN: 52.8 |

*Those that were statistically more resistant than the mother clone.

The following table identifies clones regenerated from 'Lemhi' callus lines that were not carried through the melanin precursor in vitro selection screening procedure. This population represents the distribution of blackspot resistant variants one could expect from the in vitro screening without melanin precursor. It can be seen that the tissue culture process itself increases the number of blackspot resistant Lemhi clones since Lemhi in nature normally shows relatively little, if any, resistance.

Blackspot reaction in a population of tissue cultured screened 'Lemhi' clones

| | BLACKSPOT INDEX | | |
|---|---|---|---|
| CLONE ID | Year 1 | Year 2 | Year 3 |
| 84-39 | | 182.7 | |
| 92-10 | 1.2* | | |
| 84-114 | 3.5* | 5.0* | 55.0* |
| 84-210B | 5.4* | 98.5 | 102.8 |
| 84-196 | 10.6* | 144.2 | 62.6 |
| 84-117 | 11.4* | 60.4 | 13.0* |
| 84-256 | 12.1* | 78.8 | 83.1 |
| 84-254 | 16.7* | 102.3 | 47.7* |
| 84-8 | 20.7* | | |
| 84-148 | 42.6 | 97.9 | 126.8 |
| 84-16 | 42.6 | 113.1 | 163.3 |
| 84-305 | 47.9 | 158.6 | 172.3 |
| 92-25 | 64.1 | 53.2* | 19.2* |
| 84-231 | 101.0 | 29.5* | |
| 84-155 | 105.0 | 36.2* | |
| 84-1 | 106.4 | 151.4 | 180.7 |
| 84-5 | 121.7 | 206.4 | 218.8 |
| 84-143 | 141.3 | 255.9 | 163.3 |
| 84-9 | 160.2 | 133.6 | 101.3 |
| 84-63 | 203.3 | 137.2 | 188.8 |
| 81-1 | 237.2 | 135.1 | 161.3 |
| 84-249 | | 236.6 | |
| 84-329 | | 181.9 | |
| 84-163 | | 125.5 | |
| 84-31 | | 99.2 | |
| 84-184 | 70.9 | 98.7 | 69.8 |
| 84-278 | 79.5 | 84.8 | |
| 84-351A | | 74.6 | |
| 84-27 | | 73.2 | 60.5 |
| 84-20 | | 69.2 | |
| 84-314 | | 50.9* | 105.7 |
| 84-492 | | 46.1* | 113.9 |
| 84-393 | | 46.0* | 105.1 |
| 84-459 | | 24.9* | 50.5* |
| 84-78 | | 0.4* | 1.2* |
| 92-3 | | 125.0 | |

-continued

| CLONE ID | BLACKSPOT INDEX | | |
|---|---|---|---|
| | Year 1 | Year 2 | Year 3 |
| 115-3 | | 103.6 | 103.2 |
| 91-64 | | 39.1* | |
| 81-8 | | 36.3* | |
| 120-11 | | 1.7* | |
| 84-402 | | | 199.5 |
| 84-166 | | | 47.3* |
| Lemhi MC (protoplast source) | 51.5 | 124.1 | 147.4 |
| Lemhi (state seed meristem program) | 47.9 | 94.5 | 160.5 |

\* = Significantly more resistant than the cultivar Lemhi (p = 0.05)
Year 1 data based upon 1 bruise testing experiment (5 tubers)
Year 2 data based upon 3 bruise testing experiments (15 tubers)
Year 3 data based upon 1 bruise testing experiment (5 tubers)

These results demonstrate that variation in blackspot susceptibility readily occurs and somaclones with enhanced resistance to blackspot bruise can be found in a screened population of 'Lemhi' somaclones.

The following table identifies clones regenerated from 'Lemhi' callus lines that were carried through the melanin precursor in vitro screening procedure with no blackening response. These clones were screened at various stages as shown below.

Blackspot reaction in a population of 'Lemhi' clones screened in vitro with melanin precursors (tyrosine or caffeic acid (CA))

| CLONE ID | SCREENING STAGES (Stage at which Melanin Precursor added) | | | | | BLACKSPOT INDEX | | |
|---|---|---|---|---|---|---|---|---|
| | | | | | | Year 1 | Year 2 | Year 3 |
| L-DB27 (CA) | 1 | 2 | 3 | 4 | | 0.0* | 68.3 | 53.0* |
| L-DB23 (CA) | 1 | 2 | 3 | 4 | | 1.2* | 83.6 | 75.9 |
| L-DB14 (CA) | 1 | 2 | 3 | 4 | | 3.0* | 27.6* | 93.0 |
| L-DB18 (CA) | 1 | 2 | 3 | 4 | | 3.4* | 90.6 | 105.2 |
| L-DB21 (CA) | 1 | 2 | 3 | 4 | | 4.9* | 144.6 | 170.5 |
| L-DB24 (CA) | 1 | 2 | 3 | 4 | | 36.8 | 241.3 | |
| 92-7 (CA) | | | 3 | | | 60.5 | 109.1 | 128.6 |
| 111-6 | | 2 | 3 | | 5 | | 203.8 | 89.6 |
| 103-13 | | 2 | 3 | | 5 | | 174.5 | 69.4 |
| 111-4 | | 2 | 3 | | 5 | | 157.0 | 136.7 |
| 111-17 | | 2 | 3 | | 5 | | 107.3 | 2.5 |
| 98-2 | | 2 | 3 | | 5 | | 104.8 | |
| 94-1 | | | | | 5 | | 97.4 | 103.3 |
| 111-13 | | 2 | 3 | | 5 | | 84.4 | 51.3* |
| 97-19 | | 2 | 3 | | 5 | | 83.6 | 50.7* |
| 111-20 | | 2 | 3 | | 5 | | 77.7 | 83.2 |
| 111-12 | | 2 | 3 | | 5 | | 75.8 | |
| 111-14 | | 2 | 3 | | 5 | | 75.4 | 134.4 |
| 98-1 | | 2 | 3 | | 5 | | 66.6 | |
| 103-3 | | 2 | 3 | | 5 | | 62.6 | 106.3 |
| 91-95 | | | | | 5 | | 55.3* | 33.8* |
| 97-18 | | 2 | 3 | | 5 | | 53.6* | 21.0* |
| 97-26 | | 2 | 3 | | 5 | | 46.6* | 36.1* |
| 111-3 | | 2 | 3 | | 5 | | 45.6* | 100.8 |
| 91-13 | | | | | 5 | | 42.1* | 54.7* |
| 103-2 | | 2 | 3 | | 5 | | 41.7* | 199.4 |
| 111-28 | | 2 | 3 | | 5 | | 38.5* | 94.8 |
| 92-67 | | | | | 5 | | 35.3* | 15.3 |
| L-DB4 | 1 | 2 | 3 | 4 | | | 31.8* | |
| 91-62 | | | | | 5 | | 23.8* | 59.2* |
| L-DB6 | 1 | 2 | 3 | 4 | | | 18.6* | 35.1* |
| 91-28 | | | | | 5 | | 15.2* | |

-continued

| CLONE ID | SCREENING STAGES (Stage at which Melanin Precursor added) | | | | | BLACKSPOT INDEX | | |
|---|---|---|---|---|---|---|---|---|
| | | | | | | Year 1 | Year 2 | Year 3 |
| L-DB25 (CA) | 1 | 2 | 3 | 4 | | | 14.6* | 2.5* |
| 114-8 | | 2 | 3 | | 5 | | 13.4* | 83.8* |
| 97-30 | | 2 | 3 | | 5 | | 9.5* | 132.9 |
| 92-66 | | | | | 5 | | 2.5* | |
| 91-7 | | | | | 5 | | 1.9* | |
| L-DB22 (CA) | 1 | 2 | 3 | 4 | | | 0.5* | |
| 115-1 | | 2 | 3 | | 5 | | 0.4* | 57.5 |
| 111-33 | | | 3 | | 5 | | 0.1* | 55.8 |
| 84-515 | | | | | 5 | | | |
| L-DB19 (CA) | 1 | 2 | 3 | 4 | | | | 114.4 |
| 114-5 | | 2 | 3 | 4 | 5 | | | 102.0 |
| 111-38 | | 2 | 3 | | 5 | | | 99.1 |
| 97-43 | | | 3 | | | | | 95.5 |
| 110-17 | | | 3 | 4 | 5 | | | 72.6 |
| 97-17 | | | 3 | | 5 | | | 63.5 |
| 97-44 | 1 | | 3 | | 5 | | | 57.7 |
| 91-14 | | | | | 5 | | | 38.9* |
| 103-14 | | 2 | 3 | | | | | 33.1* |
| 91-61 | | | | | 5 | | | 32.3* |
| L-DB15 (CA) | 1 | 2 | 3 | 4 | | | | 31.1* |
| 97-12 | | | 3 | | 5 | | | 27.6* |
| 91-12 | | | | | 5 | | | 26.9* |
| 111-37 | | 2 | 3 | | 5 | | | 22.4* |
| 98-5 | | | 3 | 4 | 5 | | | 21.2* |
| 115-2 | | | | | | | | 14.1* |
| 111-29 | | 2 | 3 | 4 | 5 | | | 11.8* |
| Lemhi MC (protoplast source) | | | | | | 51.5 | 124.1 | 147.4 |
| Lemhi (state seed meristem source) | | | | | | 47.9 | 94.5 | 160.5 |

*Significantly more resistant than the cultivar Lemhi (p = 0.05)
Year 1 data based upon 1 bruise testing experiment (5 tubers)
Year 2 data based upon 3 bruise testing experiments (15 tubers)
Year 3 data based upon 1 bruise testing experiment (5 tubers)

The following clones were regenerated from 'Lemhi' callus lines that were carried though the melanin precursor in vitro screening procedure with a blackening response in at least one stage.

| CLONE ID | SCREENING STAGES | | | | BLACKSPOT INDEX | | |
|---|---|---|---|---|---|---|---|
| | | | | | Year 1 | Year 2 | Year 3 |
| 111-15 | 2 | 3 | | 5 | | 133.4 | |
| 103-1 | 2 | 3 | | 5 | | 121.2 | 30.2* |
| 110-2 | | 3 | | 5 | | 75.4 | |
| 91-51 | | | | 5 | | 57.7 | |
| 111-11 | 2 | 3 | | 5 | | 39.7* | |
| 97-8 | | 3 | | 5 | | 36.7* | 16.1* |
| 115-9 | 2 | 3 | | 5 | | 0.2* | 7.4* |
| 111-35 | 2 | 3 | 4 | 5 | | | 58.0 |
| 111-26 | 2 | 3 | | 5 | | | 28.4* |
| 92-125 | | | | 5 | | | 35.6* |
| Lemhi Mother Clone (protoplast source) | | | | | 51.5 | 124.1 | 147.4 |
| Lemhi (state seed meristem source) | | | | | 47.9 | 94.5 | 160.5 |

\* = Significantly more resistant than the cultivar Lemhi (p = 0.05)
Year 1 data based upon 1 bruise testing experiment (5 tubers)
Year 2 data based upon 3 bruise testing experiments (15 tubers)
Year 3 data based upon 1 bruise testing experiment (5 tubers)

These results demonstrate that susceptibility to blackspot bruise can be identified in an in vitro selected population of somaclones and suggest that the proportion of clones with resistance to blackspot can be increased by screening the material while in tissue culture.

Conclusion

Source germplasm 'Lemhi' was generally less susceptible to bruising than in past years. 'Lemhi' is normally highly susceptible with BI values of 250–300 expected. In contrast, the average BI of 'Lemhi' tubers grown in year 1 was 51.1, in year 2, the average BI was 124.1, and in year 3 147.4. This demonstrates how closely expression of this disorder can be tied to environmental conditions and physiology of the plant. The blackspot response of 'Lemhi' is used as a comparative means of evaluating the somaclones.

It is clear that clones showing elevated resistance to blackspot bruising can be obtained via in vitro selection. A functioning in vitro screening system for blackspot resistance could prove to be a factor in how this disorder is controlled. Implementation of such a system would be significant because a large proportion of somaclones with elevated resistance to blackspot could be identified. This would greatly increase the likelihood of obtaining clones possessing all the important characteristics of the original cultivar. The probability of finding somaclones showing improvements in other traits in addition to blackspot resistance would be increased as well.

Although a particular embodiment of the invention has been described in detail for purposes of illustration, various modifications may be made without departing from the spirit and scope of the invention. Accordingly, the invention is not to be limited, except as by the appended claims.

We claim:

1. Potato plants of the Lemhi Russet variety regenerated in accordance with a method for in vitro selection of blackspot resistant tubers from regenerated Lemhi Russet potato plants obtained from tissue culture, said method comprising the steps of:

(a) culturing tissue obtained from said potato plants in cell layer medium and associated reservoir medium;

(b) subculturing said tissue on callus proliferation medium to obtain callus formation;

(c) subculturing said callus on shoot induction medium to obtain shoot formation;

(d) subculturing said shoot on a rooting medium to ensure root formation, whereby potato plants are regenerated from which blackspot resistant tubers are produced; and (e) adding at least one melanin precursor to at least one of said reservoir, callus proliferation, and rooting media, whereby said potato plants are regenerated from the calli and roots which show no blackening response when the melanin precursor is added.

2. Blackspot resistant potato tubers derived from the regenerated potato plants of claim 1.

3. Potato plants of the Lemhi Russet variety regenerated in accordance with a method of screening for blackspot resistant tubers from Lemhi Russet potato plants regenerated from tissue culture, said method comprising the steps of:

(a) culturing tissue obtained from said potato plants in cell layer medium and associated reservoir medium having an effective amount of at least one melanin precursor added thereto to cause blackening in non-resistant plants;

(b) subculturing said tissue to obtain callus formation on callus proliferation medium to which at least one melanin precursor has been added in an effective amount;

(c) transferring said calli to fresh callus proliferation medium to which at least one melanin precursor has been added in an effective amount to cause blackening in non-resistant plants;

(d) wounding said calli;

(e) selecting the calli that show no blackening response and transferring them to shoot induction medium to obtain shoot information;

(f) subculturing said shoot on rooting medium to ensure root formation for regenerating plants, an effective amount of at least one melanin precursor added to the rooting medium to cause blackening in non-resistant plants; and (g) selecting the shoots with roots which show no blackening response and transferring said regenerated plants to a suitable location to produce tubers.

4. Blackspot resistant potato tubers derived from the regenerated potato plants of claim 3.

* * * * *